US00PP07883P

United States Patent [19]

Fruehwirth

[11] Patent Number: Plant 7,883

[45] Date of Patent: Jun. 9, 1992

[54] POINSETTIA PLANT '456'

[75] Inventor: Franz Fruehwirth, Encinitas, Calif.

[73] Assignee: Paul Ecke Ranch, Inc., Encinitas, Calif.

[21] Appl. No.: 528,233

[22] Filed: May 24, 1990

[51] Int. Cl.[5] ..... A01H 5/00

[52] U.S. Cl. ..... Plt./86

[58] Field of Search ..... Plt./86, 86.3

[56] References Cited

U.S. PATENT DOCUMENTS

P.P. 4,235 4/1978 Gutbier ..... Plt. 86

P.P. 6,150 4/1988 Hrebeniuk ..... Plt. 86

4,724,276 2/1988 Ecke, Jr. ..... 47/58

*Primary Examiner*—Howard J. Locker

*Attorney, Agent, or Firm*—Arnold, White & Durkee

[57] ABSTRACT

Poinsettia, cultivar '456' is an induced by mutation cultivar, 'H518' (U.S. Plant Pat. No. 6,150) with dark red flower bracts and dark green foliage. It branches more freely than 'H518', but retains the same desirable flower and foliage characteristics. The plant height of '456' is somewhat shorter than that of 'H518'. The relative shortness of '456' offers certain economic advantages over 'H518', in that, less growth retarding chemicals need to be used to control plant height.

1 Drawing Sheet

BACKGROUND OF THE NEW PLANT

This new poinsettia cultivar originated as a sport induced by mutation of the cultivar 'H518' in a greenhouse in Encinitas, Calif. It was selected because of its dark flower bracts, dark green foliage, compact growth habit and self-branching traits which distinguish it from other poinsettia cultivars, and seem to make it a desirable plant for commercial greenhouse production. The new cultivar differs from Gutbier V-10, for example, in that the color intensity of the foliage and the bracts is significantly greater. Under post-production environments, there is much better leaf and bract retention in cultivar '456' compared with 'V-10'. After selection, stem cuttings of cultivar '456' were vegetatively reproduced for test purposes in Encinitas, Calif., and clones of the plant were subjected to successive generations of vegetative propagation which demonstrated that its distinct characteristics hold true from generation to generation.

DESCRIPTION OF THE PHOTOGRAPHS

Poinsettia '456' is illustrated in the accompanying color photographs. The upper photo is a side view of '456', one plant pinched with several flowering branches. The lower photo is a top view of the same plant showing flower and bract formation. The bract color of the photographs is somewhat lighter than the true color, because of light reflectance.

DESCRIPTION OF THE PLANT

The following is a detailed description of this new poinsettia as observed in my greenhouse in Encinitas, Calif., during December 1989. Recorded observations from flowering plants, grown as one pinched plant per pot, were observed. The pot was 14 cm. in diameter and 11 cm. in height. Color designations were compared to the 1986 edition of R.H.S. Colour Chart, first published in 1966 by the Royal Horticultural Society, London, England.

THE PLANT

Origin: Sport of 'H518'. The sport was induced by application of the procedures set forth in U.S. Pat. No. 4,724,276 to the parent plant 'H518'.

Classification:

*Botanic.*—*Euphorbia pulcherrima* Willd.

*Common name.*—Poinsettia.

*Cultivar name.*—'456'.

Form: Shrub.

Height: Short to medium, somewhat shorter than 'H518'.

Growth habit: As a single stemmed plant, upright and vigorous with several self-branching axillary stems. The application of a chemical growth retardant may not be needed to restrict height for commercial pot plant production. Observation of one plant branched in a pot with an overall height of 40 cm. and an overall width of 48 cm was made. The bract diameter of individual flowers was 28 cm.

Branching: Branching can be enhanced by removal of the stem tip. Then, several flowering branches with equal vigor will develop on a single plant. Poinsettia '456', unlike its parent plant 'H518', has a self-branching traits. Axillary branches will develop and terminate in a flower without pinching. In contrast, axillary branches develop on the parent plant 'H518', only where terminal dominance is removed by pinching. It may be desirable to pinch '456' and remove all terminal dominance. Then, 6–8 axillary branches will develop uniformly and at a faster rate, whereas, on the parent plant 'H518', only 4 to 5 axillary branches will typically develop after pinching.

Growth rate: Rooting of stem cuttings occurs in 12–18 days under intermittent mist. The plant will flower in about ten weeks under continuous long night conditions and night temperatures of about 16–18 degrees C.

Foliage: The foliage is clean and uniformly dark green from bottom to top of the plant. The leaves are of medium size, leaf blades typically being about 12–14 cm. long and about 9–10 cm. wide with leaf petioles about 6–7 cm. long.

Leaf shape: Typical leaves are ovate with obtuse bases and acuminate tips. Leaf margins are mostly entire or slightly lobed with 1 or 2 indentations on each side of the leaf blade. The leaf shape of '456' is less serrated or lobed than the leaves of 'H518'.

Color: Upper side — Dark green, darker than RHS 139A. Under side — Green, near RHS 137B.

Retention: The foliage lasts extremely well even under low light intensities in the consumer's home.

Bracts: Generally there are 15–21 uniformly colored bracts of various sizes subtending the cyathia. The primary bracts have blades typically 15–16 cm. long and 11–12 cm. wide with petioles about 4 cm. long. Bract attitude is similar for both '456' and its parent 'H518'. Most cultural requirements are the same, such as temperature, light intensity and nutrition. However, commercially, '456' would be more acceptable as a pinched, branched plant, whereas its parent 'H518', will be more suitable for a non-pinched plant.

*Shape.*—Bracts are mostly ovate to obovate with acute bases and acuminate tips. Primary bracts are somewhat lobed with usually two indentations on either side of the bract. Secondary bracts have entire margins. The bract shape of '456' is less serrated or lobed than the bracts of 'H518'.

*Color.*—Upper side — Dark red, near RHS 45A. Under side — Red, darker than RHS 47A and near RHS 46B. The color intensity of the red bracts of '456' is not quite as bright as that of the 'H518' parent.

Flowers: Generally, 12–15 cyathia (flowers) are present when the plant is in 'full bloom'. Each cyathium is about 7–8 mm long and about 5 mm wide, green in color, and fringed with red at the distal end. Usually one and occasionally two yellow nectar cups protrude from the side of each cyathium. The flower pedicel is also green and about 5–6 mm in length. The stamens protruding from the cyathia are red. The flowers of '456' appear to be the same in every respect to those of the parent plant 'H518', except that the flower response time is slightly shorter for '456'. '456' may come to full bloom 3–5 days before 'H518'.

What is claimed is:

1. A new and distinct poinsettia cultivar, substantially as herein shown and described, characterized by its dark flower bracts, dark green foliage, short to medium height, compact growth habit and self-branching traits.

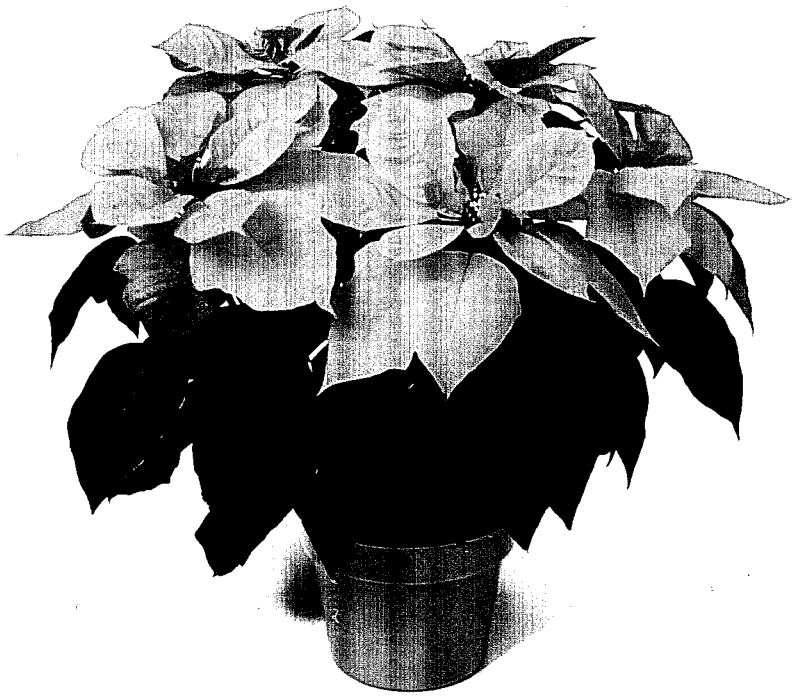
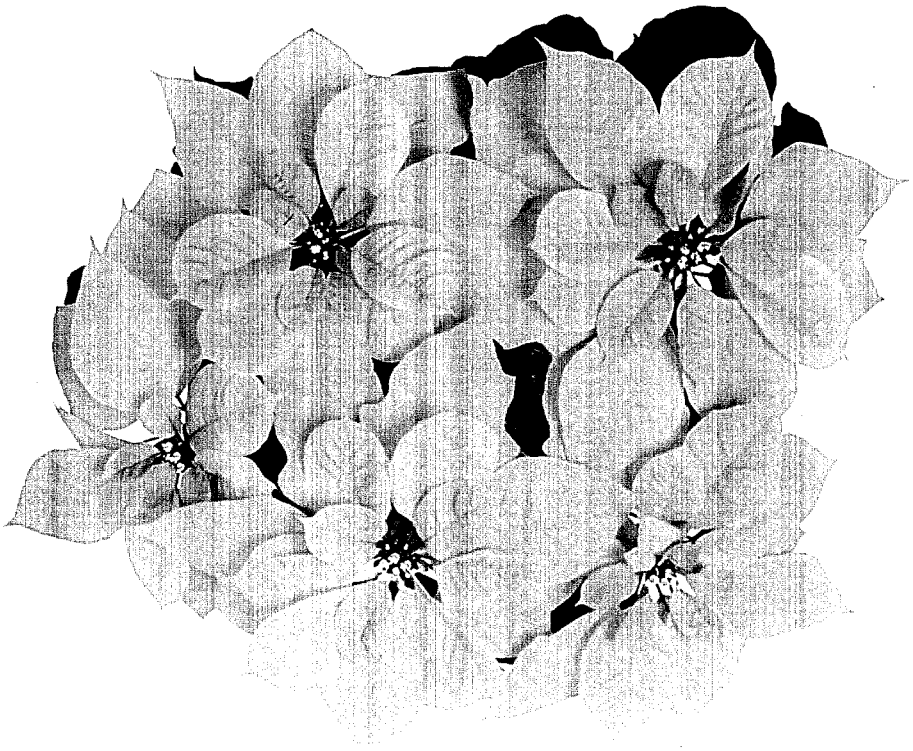

* * * * *